United States Patent [19]
Fukazawa et al.

[11] Patent Number: 4,909,989
[45] Date of Patent: Mar. 20, 1990

[54] GAS-EXCHANGE MEMBRANE FOR AN ARTIFICIAL LUNG

[75] Inventors: Hiromichi Fukazawa, Fuji; Kazuhiko Hagiwara, Fujinomiya, both of Japan

[73] Assignee: Terumo Kabushiki Kaisha (Terumo Corporation), Tokyo, Japan

[21] Appl. No.: 328,763

[22] Filed: Mar. 27, 1989

Related U.S. Application Data

[63] Continuation of Ser. No. 906,100, Sep. 11, 1986, abandoned.

[30] Foreign Application Priority Data

| Sep. 13, 1985 | [JP] | Japan | 60-201788 |
| Sep. 13, 1985 | [JP] | Japan | 60-201789 |
| Sep. 13, 1985 | [JP] | Japan | 60-201792 |

[51] Int. Cl.$^4$ .............................................. A61M 1/14
[52] U.S. Cl. ................................... 422/48; 210/500.24; 210/500.27; 210/321.62; 55/16; 55/158; 128/DIG. 3; 261/DIG. 28
[58] Field of Search ............... 422/44, 48; 128/DIG. 3; 261/DIG. 28; 55/16, 158; 210/321.62, 321.71, 321.81, 321.9, 500.23, 500.24, 500.27, 506, 508

[56] References Cited

U.S. PATENT DOCUMENTS

| 4,093,515 | 6/1978 | Kolobow . | |
| 4,239,729 | 12/1980 | Hasegawa et al. | 422/48 |
| 4,374,802 | 2/1983 | Fukasawa | 210/321.3 X |
| 4,619,897 | 10/1986 | Hato et al. | 435/177 X |

FOREIGN PATENT DOCUMENTS

| 164025 | 12/1985 | European Pat. Off. . |
| 44267 | 3/1984 | Japan . |
| 106466 | 6/1985 | Japan . |
| 2072047 | 9/1981 | United Kingdom . |

Primary Examiner—Barry S. Richman
Assistant Examiner—Lynn M. Kummert
Attorney, Agent, or Firm—Cushman, Darby & Cushman

[57] ABSTRACT

In a membrane type artificial lung using as gas-exchange membranes porous hydrophobic membranes having a wall thickness in the range of 5 to 80 μm, a porosity in the range of 20 to 80%, and a pore diameter in the range of 0.01 to 5 μm, the minute pores of the membranes are blocked with minute particles of silica having a diameter smaller than the pore diameter and having a hydrophobic surface at least on the sides thereof intended for exposure to blood. Optionally, the gas-exchange membranes have the surfaces for exposure to blood coated with a biocompatible hydrophobic resin.

20 Claims, 4 Drawing Sheets

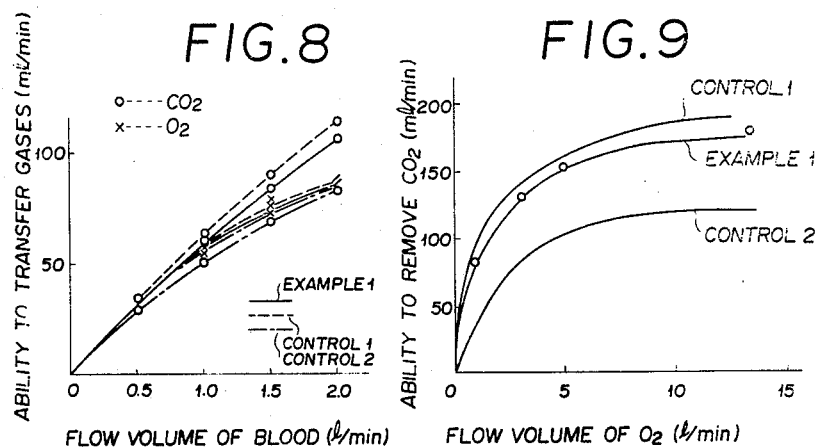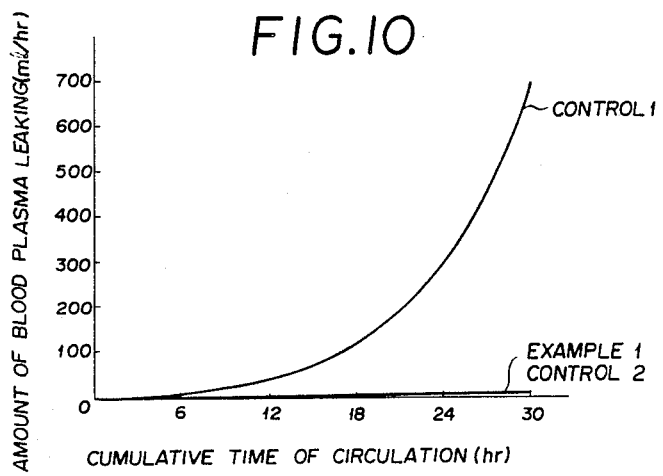

GAS-EXCHANGE MEMBRANE FOR AN ARTIFICIAL LUNG

This is a continuation of application Ser. No. 906,100, filed Sept. 11, 1986, which was abandoned upon the filing hereof.

BACKGROUND OF THE INVENTION

1. Field of the Invention:

This invention relates to a membrane type artificial lung and to a method for the manufacture thereof. More particularly, it relates to a membrane type artificial lung adapted to remove carbon dioxide gas from the blood and add oxygen to the blood during the extra-corporeal circulation of blood. The artificial lung excels in gas-exchange ability, particularly in the ability to remove carbon dioxide gas, which precludes the possibility of leakage of blood plasma even during a protracted service, exhibits high biocompatibility, and experiences a minimal loss of platelets, and to a method for the manufacture thereof.

2. Description of the Prior Art:

Heretofore, as an auxiliary means for a cardiotomy, a membrane type artificial lung is adapted to effect the exchange of gases by exposing the blood in circulation to an oxygen-containing gas through the medium of a gas-exchange membrane possessed of a satisfactory permeability to gas has been known. This gas-exchange membrane is required, in addition to having satisfactory permeability to gas, to exhibit high mechanical strength, to avoid inducing leakage of blood plasma during a protracted circulation of blood, and does not inflict on the blood any injury manifested in the form of blood coagulation, formation of microthrombosis, loss of platelets, degeneration of blood plasma proteins, or hemolysis. The gas-exchange membranes which are currently used in the membrane type artificial lungs are of two major types; homogeneous membranes and porous membranes. As homogeneous membranes, silicone membranes are predominantly used. In contrast, porous membranes are made of various materials such as, for example, polyethylene, polypropylene, polytetrafluoroethylene, polysulfones, polyacrylonitrile, polyurethane, and polyamides. The homogeneous silicone membranes, owing to a deficiency in strength, are not produced in any smaller wall thickness than 100 μm, and therefore possess limited permeability to gas, and are particularly deficient in permeability to carbon dioxide gas. When tens of thousands of hollow fiber membranes of silicone are bundled to acquire a desired gas-exchange ability and the bundle is used in place of a plain homogeneous silicone membrane, the apparatus using this bundle proves disadvantageous in that the apparatus has to be large in order to accommodate the bundle, the volume of priming is proportionately large, and the bundle is costly. The porous membranes possess numbers of minute pores penetrating the membranes in the direction of wall thickness. Since the membranes are hydrophobic, they do not permit the passage of blood plasma through the minute pores thereof, namely they do not experience leakage of blood plasma therethrough from the blood conduit side to the gas conduit side, and they accordingly permit the addition of oxygen from the feed gas to the blood and the removal of carbon dioxide gas from the blood into the effluent gas. The porous membranes, however, are degraded by dew because of their high permeability to steam, and at times experience leakage of blood plasma during a protracted use in blood circulation. This phenomenon is witnessed even in porous membranes which in a test for water leakage conducted during the course of the manufacture of artificial lungs, which were confirmed to be free from such problems. Thus, this is a phenomenon which takes place during use. Only a few of the materials of which the porous membranes are made are satisfactory from the viewpoint of the biocompatibility, as evidenced by the loss of platelets.

For the purpose of overcoming the various drawbacks of the porous membrane as described above, we have proposed an artificial lung having the minute pores in the porous membrane blocked with silicone oil (Japanese Patent Application SHO No. 58(1983)-92,325) and an improved artificial lung having the minute pores in the porous membrane blocked with silicone rubber (Japanese Patent Application SHO No. 59(1984)-105,384). The artificial lung having the minute pores in the porous membrane blocked with silicone rubber has eliminated the problem of blood plasma leakage experienced by the conventional artificial lung using an ordinary porous membrane. In terms of the ability to remove carbon dioxide gas, however, the artificial lung is not satisfactory. For example, it has effected the removal of the amount of carbon dioxide gas produced at all in the patient's living body with a small amount of extra-corporeal circulation of the blood as in $ECCO_2R$ (extra-corporeal $CO_2$ removal) with difficulty.

An object of this invention, therefore, is to provide a novel membrane type artificial lung and a method for the manufacture thereof.

Another object of this invention is to provide a membrane type artificial lung capable of removing carbon dioxide gas from the blood and adding oxygen to the blood during the extra-corporeal circulation of the blood, in which the membrane type artificial lung excels in the ability to exchange gases, precludes the possibility of leakage of blood plasma during a protracted use, exhibits high biocompatibility, experiences the loss of platelets only nominally and a method for the manufacture thereof.

Yet another object of this invention is to provide a membrane type artificial lung most suitable for $ECCO_2R$ and a method for the manufacture thereof.

SUMMARY OF THE INVENTION

The objects described above are accomplished by a membrane type artificial lung using porous hydrophobic membranes having a wall thickness in the range of 5 to 80 μm, a porosity in the range of 20 to 80%, and a pore diameter in the range of 0.01 to 5 μm as gas-exchange membranes, in which the artificial lung is characterized in that the pores of the gas-exchange membranes are blocked with minute particles of a diameter smaller than the diameter of the pores and at least the surfaces of the gas-exchange membranes exposed to the blood in circulation are hydrophobic.

This invention discloses a membrane type artificial lung, wherein the gas-exchange membranes are hollow fiber membranes. This invention also discloses a membrane type artificial lung, wherein the hollow fiber membranes have an inside diameter in the range of 100 to 1,000 μm. This invention further discloses a membrane type artificial lung, wherein the pores are blocked by being filled with minute particles. This invention discloses a membrane type artificial lung, wherein the minute particles are made of a hydrophobic substance. This invention also discloses a membrane type artificial lung, wherein the minute particles are made of a hydrophilic substance and at least the surfaces of the minute particles exposed to the blood are coated with a hydrophobic substance. This invention further discloses a membrane type artificial lung, wherein the gas-exchange membranes are made of an olefin type resin. This invention discloses a membrane type artificial lung, wherein the gas-exchange membranes are made of polypropylene. This invention further discloses a membrane type artificial lung, wherein the minute particles have a diameter approximately in the range of 0.003 to 1.0 μm.

The objects described above are accomplished by a membrane type artificial lung using porous hydrophobic membranes having a wall thickness in the range of 5 to 80 μm, a porosity in the range of 20 to 80%, and a pore diameter in the range of 0.01 to 5 μm as gas-exchange membranes, which artificial lung is characterized in that the pores of the gas-exchange membranes are blocked with minute particles of a diameter smaller than the diameter of the pores and at least the surfaces of the gas-exchange membranes exposed to the blood in circulation are coated with a hydrophobic resin possessing biocompatibility.

This invention discloses a membrane type artificial lung, wherein the air flux is not more than 500 ml/min.m$^2$.mmHg. This invention also discloses a membrane type artificial lung, wherein the gas-exchange membranes are hollow fiber membranes. This invention further discloses a membrane type artificial lung, wherein the hollow fiber membranes have an inside diameter in the range of 100 to 1,000 μm. This invention discloses a membrane type artificial lung, wherein the pores are blocked by being filled with minute particles. This invention also discloses a membrane type artificial lung, wherein the minute particles are made of silica. This invention further discloses a membrane type artificial lung, wherein the minute particles have a diameter approximately in the range of 0.003 to 1.0 μm. This invention discloses a membrane type artificial lung, wherein the biocompatible hydrophobic resin is a fluorine-containing resin. This invention discloses a membrane type artificial lung, wherein the biocompatible hydrophobic resin is a vinyl type copolymer having as one component thereof a vinyl monomer possessing a perfluoroalkyl side chain. This invention also discloses a membrane type artificial lung, wherein the biocompatible hydrophobic resin is a vinyl type block copolymer. This invention further discloses a membrane type artificial lung, wherein the vinyl type block copolymer is a methacrylate type copolymer having as one component thereof a methacrylate monomer possessing perfluoroalkyl side chain. This invention discloses a membrane type artificial lung, wherein the weight ratio in the block copolymer of the polymer component formed of the vinyl monomer possessing a perfluoroalkyl side chain to the polymer component formed of the other monomer of the copolymer falls in the range of 0.25 to 1.5. This invention also discloses a membrane type artificial lung, wherein the perfluoroalkyl side chain is $CH_2CH_2(CF_2)_2CF_3$. This invention further discloses a membrane type artificial lung, wherein the coating of biocompatible hydrophobic resin has a wall thickness in the range of 0.001 to 10 μm. This invention discloses a membrane type artificial lung, wherein the gas-exchange membrane is made of an olefin type resin. This invention also discloses a membrane type artificial lung, wherein the gas-exchange membrane is made of polypropylene.

The objects described above are accomplished by a method for the manufacture of an artificial lung using as a gas-exchange membrane a porous membrane having a wall thickness in the range of 5 to 80 μm, a porosity in the range of 20 to 80%, and a pore diameter in the range of 0.01 to 5 μm, which method, is characterized by a dispersion of minute particles having a diameter smaller than the diameter of the minute pores to be filtered through the porous membrane thereby blocking the minute pores of the porous membrane with the minute particles and then removing part of the dispersion remaining in the surface region of the porous membrane with a cleaning liquid.

This invention discloses a method for the manufacture of a membrane type artificial lung, wherein the minute particles are made of a hydrophobic substance. This invention also discloses a method for the manufacture of a membrane type artificial lung, wherein the minute particles are made of a hydrophilic substance and, after the minute pores have been blocked with the minute particles, at least the surfaces of the minute particles exposed to the blood are subjected to a treatment for imparting hydrophobicity. This invention further discloses a method for the manufacture of a membrane type artificial lung, wherein the treatment for imparting hydrophobicity is effected by bringing a hydrophobic resin solution into contact with at least the surfaces of the minute particles exposed to the blood, removing the resin solution adhering to the portions other than the minute particles with a cleaning liquid incapable of dissolving the hydrophobic resin, and subsequently vaporizing the solvent thereby forming a coating of the hydrophobic resin on the surfaces of the minute particles exposed to the blood. This invention discloses a method for the manufacture of a membrane type artificial lung, wherein the porous membranes are porous hydrophobic membranes, which are rendered hydrophilic through contact with an alcohol, and the resulting porous hydrophilic membranes filter a dispersion of minute particles using water as a dispersion medium. This invention also discloses a method for the manufacture of a membrane type artificial lung, wherein hollow fiber porous membranes having a wall thickness in the range of 5 to 80 μm, a porosity in the range of 20 to 80%, a pore diameter in the range of 0.01 to 5 μm, and an inside diameter in the range of 100 to 1,000 μm are used as gas-exchange membranes, and a dispersion of minute particles having a diameter smaller than the diameter of the minute pores is allowed to flow into the interiors of the hollow fiber porous membranes and filter through the walls thereof so as to block the minute pores in the hollow fiber porous membranes with the minute particles, and the part of the dispersion remaining inside the hollow fiber porous membranes is removed with a cleaning liquid. This invention further discloses a method for the manufacture of a membrane type artificial lung, wherein the interiors of the hollow fiber porous membranes are subjected to application of pressure during the course of filtration. This invention discloses a method for the manufacture of a membrane type artificial lung, wherein the hollow fiber porous membranes ensure flow of a fluid in the axial direction thereof during the course of the filtration. This invention also discloses a method for the manufacture of a membrane type artificial lung, wherein the minute particles are made of silica. This invention further discloses a method for the manufacture of a membrane type artificial lung, wherein the gas-exchange membranes are made of an olefin type resin. This invention discloses a method for the manufacture of a membrane type artificial lung, wherein the gas-exchange membranes are made of polypropylene.

The objects described above are further accomplished by a method for the manufacture of an artificial lung using porous membranes having a wall thickness in the range of 5 to 80 μm, a porosity in the range of 20 to 80%, and a pore diameter in the range of 0.01 to 5 μm as gas-exchange membranes, which method is characterized by causing a dispersion of minute particles having a diameter smaller than the diameter of the minute pores to be filtered through the porous membranes thereby blocking the minute pores of the porous membranes with the minute particles, removing the part of the dispersion remaining in the surface portion of the porous membranes with a cleaning liquid, bringing a solution of a biocompatible hydrophobic resin into contact with at least the surfaces of the porous membranes exposed to the blood, and then vaporizing the solvent thereby coating at least the surfaces of the porous membranes exposed to the blood with the resin.

This invention discloses a method for the manufacture of a membrane type artificial lung, wherein the porous membranes are porous hydrophobic membranes, the porous hydrophobic membranes are rendered hydrophilic through contact with an alcohol, and the resulting porous hydrophilic membranes filter a dispersion of minute particles using water as a dispersion medium. This invention also discloses a method for the manufacture of a membrane type artificial lung, wherein hollow fiber porous membranes having a wall thickness in the range of 5 to 80 μm, a porosity in the range of 20 to 80%, a pore diameter in the range of 0.01 to 5 μm, and an inside diameter in the range of 100 to 1,000 μm are used as gas-exchange membranes, a dispersion of the minute pores is caused to flow into the interiors of the hollow fiber porous membranes and filter through the walls thereof and, consequently block the minute pores of the hollow fiber porous membranes with the minute particles, the part of the dispersion remaining inside the hollow fiber porous membranes is removed with a cleaning liquid, a solution of biocompatible hydrophobic resin to flow in the interiors of the hollow fiber porous membranes, and the solvent is vaporized so as to coat at least the surfaces of the hollow fiber porous membranes exposed to the blood with the resin. This invention further discloses a method for the manufacture of a membrane type artificial lung, wherein the interiors of the hollow fiber porous membranes are subjected to application of pressure during the course of filtration. This invention discloses a method for the manufacture of a membrane type artificial lung, wherein the hollow fiber porous membranes are caused to ensure flow of a fluid in the axial direction thereof during the course of filtration. This invention further discloses a method for the manufacture of a membrane type artificial lung, wherein the minute particles are made of silica. This invention further discloses a method of the manufacture of a membrane type artificial lung, wherein the biocompatible hydrophobic resin is either a fluorine-containing resin or silicone rubber. This invention discloses a method for the manufacture of a membrane type artificial lung, wherein the biocompatible hydrophobic resin is a vinyl type copolymer having as one component thereof a vinyl monomer possessing a perfluoroalkyl side chain. This invention also discloses a method for the manufacture of a membrane type artificial lung, wherein the gas-exchange membranes are made of an olefin type resin. This invention further discloses a method for the manufacture of a membrane type artificial lung, wherein the gas-exchange membranes are made of polypropylene.

BRIEF DESCRIPTION OF THE DRAWINGS

FIG. 8 is a graph showing the relation between the ability to add oxygen gas and the ability to remove carbon dioxide gas on one part and the flow volume of blood through the artificial lung on the other part, FIG. 9 is a graph showing the relation between the ability to remove carbon dioxide gas and the flow volume of oxygen through the artificial lung, FIG. 10 is a graph showing the relation between the amount of blood plasma leaking and the cumulative time of extra-corporeal circulation of blood.

DESCRIPTION OF PREFERRED EMBODIMENT

This invention will be described in detail below with reference to the accompanying drawings.

Figure 1A:
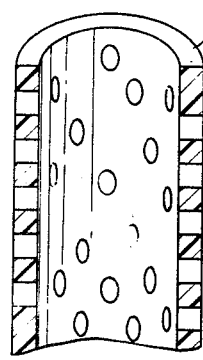
FIGS. 1A-1C are model diagrams illustrating a process for the production according to this invention and a gas-exchange membrane gradually taking shape along the course of manufacture.
Figure 1B:
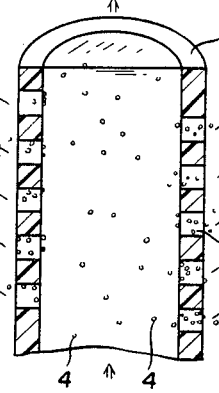
Figure 1C:
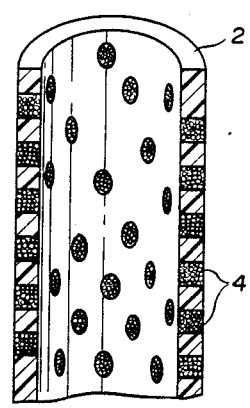

FIG. 1C is a model diagram illustrating a microstructure of a typical gas-exchange membrane in a membrane type artificial lung as one embodiment of the present invention.

Figure 2:
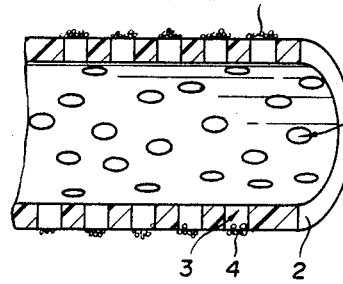
FIGS. 2 and 3 are model diagrams representing other embodiments of the present invention.
Figure 3:
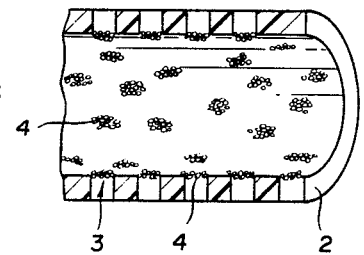

As illustrated in FIG. 1C, a gas-exchange membrane 2 in a membrane type artificial lung 1 is a hydrophobic porous membrane which has a wall thickness in the range of 5 to 80 μm, preferably 10 to 60 μm, a porosity in the range of 20 to 80%, preferably 30 to 60%, and a pore diameter in the range of 0.01 to 5 μm, preferably 0.01 to 1 μm. In the present embodiment, the gas-exchange membrane is assumed to be in the shape of a hollow fiber having an inside diameter in the range of 100 to 1,000 μm, preferably 100 to 300 μm. The individual minute pores 3 in the gas-exchange membrane 2 are blocked with minute particles 4 having at least the surfaces thereof for contact with the blood rendered hydrophobic. At least the surface of the gas-exchange membrane 2 which has the minute pores thereof blocked with minute particles 4, therefore, is retained in a hydrophobic state. The minute pores 3, in the present invention, are blocked by having the interiors of the minute pores 3 filled up with the minute particles 4. Alternatively, the minute pores 3 may be blocked by having the minute particles 4 applied fast as with adhesive agent to the surface parts of the minute pores 3 on the inner surface side of the gas-exchange membrane 2 as illustrated in FIG. 3 or on the outer surface side of the gas-exchange membrane 2 as illustrated in FIG. 2. Since the individual minute pores 3 are blocked with minute particles 4 as described above, it follows that the gas-exchange membrane 2 is allowed to possess extremely minute pores not discernible on the electron-microscope level.

As the material for the gas-exchange membranes 2, a hydrophobic macromolecular substance such as polypropylene, polyethylene, polytetrafluoroethylene, polysulfone, polyacrylonitrile, or cellulose acetate can be used. Among other materials enumerated above, polyolefin type resins prove desirable and polypropylene proves particularly desirable. A polypropylene membrane having minute pores formed therein by the stretching method or the solid-liquid phase separation method is the best choice.

As the material 4 for the minute particles to be used for blocking the minute pores 3 in the gas-exchange membranes 2, an inorganic substance such as silica, alumina, zirconia, magnesia, barium sulfate, calcium carbonate, a silicate, titanium oxide, silicon carbide, carbon black, or white carbon or a macromolecular latex such as polystyrene latex, styrene rubber (SBR) latex, or nitrile rubber (NBR) latex can be used. When the material for the minute particles 4 is hydrophobic, the minute particles 4 can be used in their unmodified form for the blocking of the minute pores 3. When the material for the minute particles is hydrophilic, at least the surfaces of the minute particles 4 must be coated with a hydrophobic material such as, for example, silicone before or after the minute pores 3 are blocked. The minute particles have a diameter in the range of 0.003 to 1.0 $\mu$m, preferably 0.003 to 5 $\mu$m.

Further, when the minute particles 4 are hydrophilic, the surfaces of the minute particles 4 are coated with a thin hydrophobic film of a silicone such as, for example, dimethyl polysiloxane, methylphenyl polysiloxane, methylvinyl polysiloxane, methyl phenyl vinyl polysiloxane, an aminoalkyl siloxane, or dimethyl siloxane by allowing the solution of the silicone in a halogenated hydrocarbon such as, for example, 1,1,2-trichloro-1,2,2-trifluoroethane, trichlorofluoromethane, or 1,1,2,2-tetrachloro-1,2-difluoroethane to flow in the interiors of the hollow fibers, thereafter removing the part of the silicone solution remaining inside the hollow fibers, and drying the wet hollow fibers. It is desirable that before the hollow fibers are dried, the interiors of the hollow fiber should be washed with a fluid incapable of dissolving the deposited silicone.

The blocking of the minute pores 3 in the gas-exchange membrane 2 with the minute particles 4 can be carried out as follows, for example.

First, a dispersion of minute particles 4 having a diameter smaller than the diameter of the minute pores is caused to flow, as illustrated in FIG. 1B, in the porous gas-exchange membrane 2 of a structure illustrated in FIG. 1A and filter through the porous gas-exchange membrane 2. Thus, part of the dispersion is allowed to pass through the minute pores 3 of the gas-exchange membrane 2. The minute particles 4 are applied on the gas-exchange membrane 2 in the form of the dispersion. For this dispersion, any of the dispersion media which are stable in the presence of the minute particles and the gas-exchange membrane 2 can be used. For example, water or an alcohol can be used. When the dispersion medium is water and the gas-exchange membrane 2 is hydrophobic, however it is necessary that the surface of the gas-exchange membrane should be rendered hydrophilic by contact with an alcohol such as ethanol or isopropanol before the dispersion is passed inside the membrane. Further, when the gas-exchange membrane 2 is in the shape of a hollow fiber as in the present embodiment, satisfactory passage of the dispersion of the minute particles 4 in the direction of the minute pores 3 of the gas-exchange membrane 2 is attained by increasing the resistance offered to the flow of the dispersion on the side opposite the inflow side end, e.g., the outflow side end, as by constricting the opening on the outflow side end thereby applying pressure of the order of about 1 to 3 kg/cm$^2$ on the interior of the hollow fiber gas-exchange membrane 2. Since there is the possibility that the pressure, if excessively high, will disrupt the membrane structurally, it is necessary that the hollow fiber gas-exchange membrane 2 should ensure flow of the dispersion in the axial direction thereof.

When the dispersion of the minute particles 4 is caused to flow in the gas-exchange membrane 2 and filter through the wall thereof, the minute particles 4 contained in the dispersion are caught inside the minute pores 3 of the gas-exchange membrane 2 so as to fill up the minute pores 3 much after the pattern of clogging, with the result that the minute pores will be blocked.

After the minute pores 3 of the gas-exchange membrane 2 have been blocked with the minute particles 4, the part of the dispersion which remain on the surface part of the gas-exchange membrane 2, i.e., inside the hollow fiber gas-exchange membrane 2 in the present embodiment, is removed with a cleaning fluid such as, for example, air or water. The operation of this cleaning is desired, in the present embodiment, to be effected by introducing the cleaning fluid into the membrane on the side opposite the inflow side, i.e. on the outflow side.

As the result of the blocking of the minute pores 3 of the gas-exchange membrane 2 with the minute particles 4, the gas-exchange membrane 2 is enabled to acquire extremely minute pores not discernible on the electron-microscope level. These extremely minute pores completely penetrate the gas-exchange membrane from the inner to the outer surface thereof. The treatment for blocking the minute pores 3 to be carried out as described above suffices where the minute particles 4 are hydrophobic. When the minute particles 4 are hydrophilic, however, at least the surfaces of the minute particles blocking the minute pores 3 of the gas-exchange membrane 2 which are exposed to the blood are desired to be rendered hydrophobic. This impartation of hydrophobicity is effected in the present embodiment, for example, by causing a solution of hydrophobic resin to flow inside the hollow fiber gas-exchange membrane 2 and contact at least the surfaces of the minute particles 4 exposed to the blood, removing the part of the solution adhering to the part other than the minute particles by passing a cleaning solution incapable of dissolving the hydrophilic resin through the interior of the hollow fiber gas-exchange membrane 2, and thereafter vaporising the solvent. The hydrophobic resin is desired to be a silicone resin or a fluorine-containing resin because of superiority of biocompatibility and permeability to gas. The silicone rubber is desired to be of a room temperature curing type (RTV) which may be either a one-pack composition or a two-pack composition. As the two-pack type RTV silicone, a polymer of vinyl methyl siloxane and methyl hydrogen siloxane is desirable. As the fluorine-containing resin, although polytetrafluoroethylene, polytrifluoroethylene, etc. are usable, a vinyl type copolymer having as one component thereof a vinyl monomer possessing a perfluoroalkyl side chain proves particularly desirable because of its excellence in biocompatibility and permeability to gas.

Figure 4A:
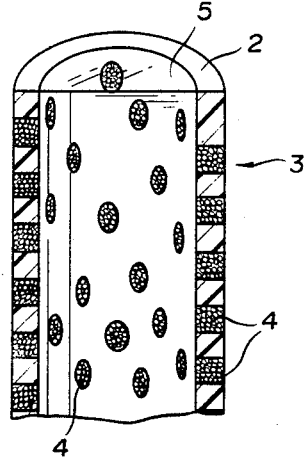
FIGS. 4A-4B are model diagrams illustrating another process for the production according with this invention and a gas-exchange membrane taking shape along the course of manufacture.
Figure 4B:
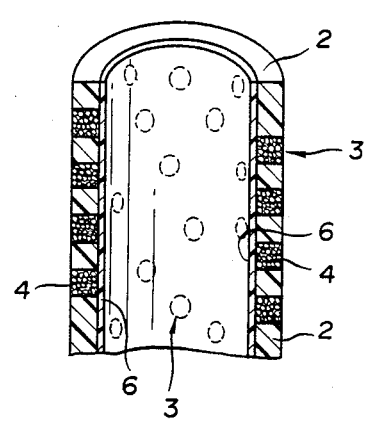

FIG. 4B is a model diagram showing the microstructure of another typical gas-exchange membrane of a membrane type artificial lung as another embodiment of this invention.

The individual minute pores 3 of the gas-exchange membrane 2, similarly to those of the embodiment of FIG. 1C, are blocked with minute particles 4 having a diameter smaller than the diameter of the minute pores. Moreover, at least the surface of the gas-exchange membrane exposed to the blood has a coating 6 of a biocompatible hydrophobic resin.

Figure 6:
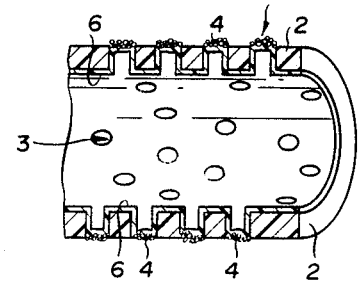
FIGS. 5 and 6 are model diagrams representing other embodiments of the present invention.
Figure 5:
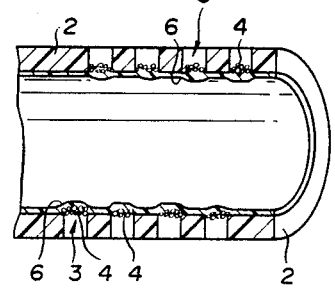

The minute pores 3 in the present embodiment are blocked in a manner having the minute particles 4 packed within the minute pores 3. Alternatively, the blocking may be attained by causing the minute particles 4 to adhere fast to the surface parts of the minute pores 3 as with adhesive agent on the inner surface side of the gas-exchange membrane 2 as illustrated in FIG. 5 or on the outer surface side of the gas-exchange membrane 2 as illustrated in FIG. 6. Because the individual minute pores 3 are blocked with the minute particles 4, it follows that the gas-exchange membrane 2 acquires extremely minute particles not discernible on the electron-microscope level and these extremely minute pores are penetrating the gas-exchange membrane from the inner to the outer surface of the gas membrane.

The method for the manufacture of the gas-exchange membrane in the present embodiment is identical with that of the preceding embodiment up to the step of blocking the individual minute pores 3 of the gas-exchange membrane 2 with the minute particles 4. The materials used for the gas-exchange membrane, the minute particles, the dispersion medium, the cleaning fluid, etc. in the present embodiment are identical with those of the preceding embodiment. The method for the second embodiment comprises the steps of blocking the individual pores of the gas-exchange membrane 2 with minute particles 4, removing the part of the dispersion of the minute particles 4 remaining on the surface part of the gas-exchange membrane with a cleaning fluid, then bringing a solution 5 of biocompatible hydrophobic resin into contact with at least the surface of the gas-exchange membrane 2 exposed to the blood as illustrated in FIG. 4A, and thereafter vaporizing the solvent thereby forming a coating 6 of the resin on at least the surface of the porous by hydrophobic gas-exchange membrane exposed to the blood as illustrated in FIG. 4B. As the biocompatible hydrophobic resin, the silicone rubber described above and the fluorine-containing resin which will be described below is preferable and particularly a vinyl type copolymer having as one component thereof a vinyl monomer possessing a perfluoroalkyl side chain is preferable. When a vinyl type copolymer having as one component thereof a vinyl monomer possessing a perfluoroalkyl side chain, for example, is used as the biocompatible hydrophobic resin, a solution having this copolymer dissolved in a concentration in the range of 1 to 10% by weight, preferably 3 to 5% by weight, is used for the coating. When a silicone rubber such as, for example, the polymer of vinylmethyl siloxane and methyl hydrogen siloxane is used as the biocompatible hydrophobic resin, a solution having the silicone rubber dissolved in a concentration in the range of 5 to 80% by weight, preferably 20 to 70% by weight is used for the coating. As the solvent for either of the solutions just mentioned, any of the typical solvents cited previously can be used.

The vinyl type copolymer having as one component thereof a vinyl monomer possessing a perfluoroalkyl side chain is a copolymer of a desired vinyl type polymer with a vinyl monomer possessing a perfluoroalkyl side chain. Preferably, this copolymer is the so-called A-B type block copolymer which has a block of a homopolymer of a vinyl monomer possessing a perfluoroalkyl side chain linked to a mother block of a desired vinyl type polymer (which may be a homopolymer, a block copolymer, or a random copolymer). Typical examples of the vinyl monomer possessing a perfluoroalkyl side chain include perfluoroacrylates and perfluoromethacrylates which possess such perfluoroalkyl groups as $-CH_2(CF_2)_2H$, $-CH_2(CF_2)_4H$, $-CH_2CF_3$, and $-CH_2CH_2(CF_2)_7CF_3$, preferably $-CH_2CH_2(CF_2)_7CF_3$, as side chains thereof. Typical examples of the vinyl monomer which forms the mother block alkyl methacrylates such as methyl methacrylate, ethyl methacrylate, butyl methacrylate, and 2-ethylhexyl methacrylate, and alkyl acrylates such as methyl acrylate, ethyl acrylate, and butyl acrylate. In the vinyl type block copolymer having as one component thereof a vinyl monomer possessing a perfluoroalkyl side chain, the weight ratio of the polymer component formed of a vinyl monomer possessing a perfluoroalkyl side chain to the other vinyl monomer of the copolymer is in the range of 0.25 to 1.5, preferably 0.3 to 1.2. If this weight ratio is not more than 0.25, there is the possibility that the microstructural phase separation necessary for inhibiting agglutination of platelets will fail to manifest. If the weight ratio exceeds 1.5, there is the possibility that the solution of the copolymer with a solvent will become difficult and the fabricability of the copolymer will be degraded. This block copolymer is obtained by preparing a vinyl type polymer intended to constitute a mother block possessing a peroxy bond in the main chain thereof and polymerizing a perfluoroacrylate by dispersion polymerization using the vinyl polymer as a polymerization initiator.

The vinyl type block copolymer having as one component thereof a vinyl monomer possessing a perfluoroalkyl side chain is soluble in organic solvents embracing ketones such as acetone, methylisobutyl ketone, methylisobutyl ketone, and cyclohexanone, alcohols such as methanol, ethanol, n-butanol, and sec-butanol, esters such as ethyl acetate and butyl acetate, ethers such as dimethylformamide, tetrahydrofuran, diethyl ether, methyl cellosolve, and ethyl cellosolve and chloroform.

When the vinyl type block copolymer having as one component thereof a vinyl monomer possessing a perfluoroalkyl side chain is used as a hydrophobic resin, a solution having the vinyl type block copolymer dissolved therein in a concentration of 1 to 10% by weight, preferably 3 to 5% by weight, is used for contact with the porous membranes. As the solvent to be used for this solution, though any of the solvents enumerated above can be adopted, it is preferable to adopt one member or a mixture of two or more members of the group aforementioned of ketones or a mixture of a ketone with an alcohol. Since it is necessary to control the vaporization of the solvent for the sake of the formation of a coating, it is proper to use a mixed solvent such as, for example, a 4/6 (volumertric ratio) mixture of methylethyl ketone/methylisobutyl ketone or a (4/6)10 (volumetric ratio) mixture of methylethyl ketone/methyl isobutyl ketone)/ethanol. When a silicone rubber such as, for example, the polymer of vinyl methyl siloxane and methyl hydrogen siloxane is used as the hydrophobic resin, a solution having the silicone rubber dissolved therein in a concentration in the range of 5 to 80% by weight, preferably 20 to 70% by weight, is used for contact with the porous membranes. This solution is left reacting and curing at a temperature in the range of 20° to 80° C., to produce a coating 6. Typical examples of the solvent usable for this solution include benzene toluene, xylene, hexane, dichloromethane, methylethyl ketone, difluoroethane, ethyl acetate, trichloroethane, and mixtures thereof. The solution, as a curing crosslinker, contains a platinum family metal in the form of element, oxide, or compound, as represented by chloroplatinic acid. Where the silicone rubber used alone has too high viscosity to permit smooth flow of the solution inside the interiors of the hollow fibers, the silicone rubber may be used in combination with a silicone oil (liquid component) such as dimethyl silicone oil, methylphenyl silicone oil, methyl chlorophenyl silicone oil, or branched dimethyl silicone oil in proportions such that the weight ratio of silicone rubber (solid component): silicone oil (liquid component) will fall approximately in the range of 2:8 to 8:2. Typical examples of the cleaning liquid usable herein embrace combinations of toluene with propylene glycol, toluene with dipropylene glycol, dichloromethane with diethylene glycol, dichloroethane with ethylene glycol, methylethyl ketone with ethylene glycol and the like.

The coating of the resin to be formed on at least the surface of the porous hydrophobic gas-exchange membrane 2 intended for exposure to blood as illustrated in FIG. 4B has a wall thickness approximately in the range of 0.001 to 10 $\mu$m, preferably 0.001 to 5 $\mu$m. If this wall thickness exceeds 10 $\mu$m, there is the possibility that the gas-exchange ability of the gas-exchange membrane 2 will be degraded and, in the case of the gas-exchange membrane which is in the shape of a hollow fiber, the flow path for blood will be contracted.

In the case of this method of manufacture, the additional treatment for impartation of hydrophobicity essentially involved in the case of the preceding method of manufacture is not required even when the minute particles blocking the minute pores of the gas-exchange membranes 2 are made of such a hydrophilic substance as silica because the surfaces intended for exposure to blood are covered with the coating 6 of biocompatible hydrophobic resin.

The manufacture of the membrane type artificial lung of this invention can be carried out by either of the methods described above. In either case, the procedure can be carried out before the artificial lung is assembled. Preferably, it is carried out after module assembly.

In the membrane type artificial lung of this invention obtained as described above, the air flux is desired to be not more than 500 ml/min.m$^2$.mmHg, preferably not more than 100 ml/min.m$^2$.mmHg. If the air flux exceeds 500 ml/min.m$^2$.mmHg, there is the possibility that the artificial lung will suffer from leakage of blood plasma during the course of a protracted use in blood circulation.

Figure 7:
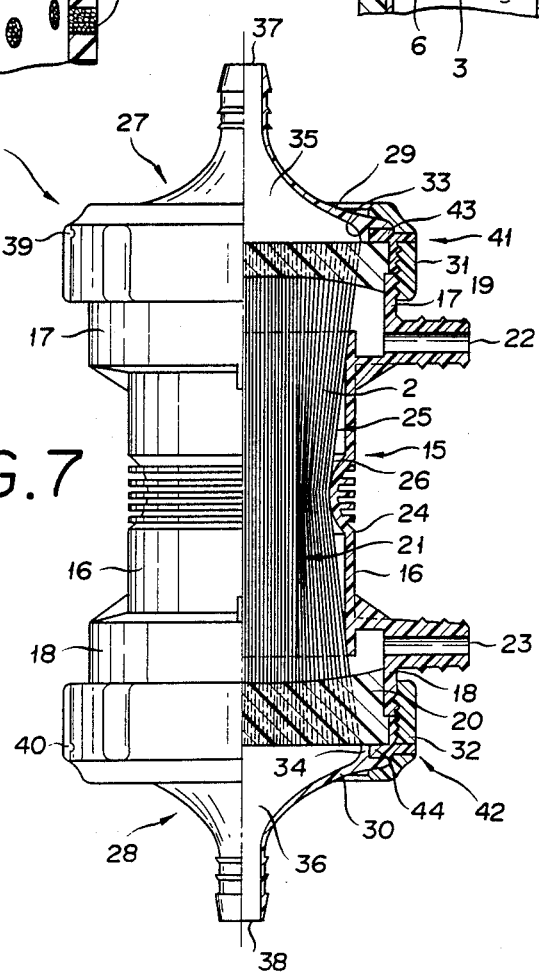
FIG. 7 is a partial cross section of a typical hollow fiber membrane type artificial lung as one embodiment of the present invention.

FIG. 7 illustrates the state in which a hollow fiber membrane type artificial lung as one embodiment of this invention is assembled. The hollow fiber membrane type artificial lung 11 is provided with a housing 15. This housing comprises a cylindrical housing body 16 and annular externally threaded fitting covers 17, 18 disposed one each at the opposite ends of the annular housing body 16. Inside the housing 15, a multiplicity of, specifically 10,000 to 60,000 hollow fiber gas-exchange membranes 2 having the minute pores thereof blocked with extremely minute particles as described above are parallelly disposed along the direction of length of the housing 15 as mutually separated and spread throughout the entire cross-sectional area of the housing 15. The opposite ends of the gas-exchange membranes 2 are water-tightly supported in position respectively with bulkheads 19, 20 inside the fixing covers 17, 18 in such a manner that their openings will remain intact.

The bulkheads 19, 20 form an oxygen chamber 21, a chamber for transfer of a first substance, jointly with the outer surfaces of the gas-exchange membranes 2 and the inner surface of the housing 15, block the oxygen chamber 21, and separate the oxygen chamber 21 from a space for passage of blood (not shown), a space for flow of a second substance, which is formed inside the aforementioned gas-exchange membranes 2.

The fixing cover 17 is provided with an inlet 22 for feeding oxygen as the fluid for transfer of the first substance. The other fixing cover 18 is provided with an outlet 23 for discharging oxygen.

Desirably on the inner surface of the cylindrical housing body 16 of the housing 15, a constricting part 24 for squeezing the bundle of gas-exchange membranes is annularly raised at the central part in the axial direction. Specifically, the constricting part 24 is integrally formed with the cylindrical housing body on the inner surface of the cylindrical housing body so as to squeeze the periphery of the hollow fiber bundle 25 comprising the multiplicity of gas-exchange membranes 2 inserted inside the cylindrical housing body 16. As the result, the hollow fiber bundle 25 is squeezed radially to form a squeezed part at the center in the axial direction as illustrated in FIG. 7. The packing ratio of gas-exchange membranes 2 varies at different parts along the axial direction and is highest at the central part. For the reason to be described afterward, desirable packing ratios at different parts are shown below. The packing ratio at the central squeezed part 26 is approximately in the range of 60 to 80%, that inside the cylindrical housing body 16 is approximately in the range of 30 to 60%, and that at the opposite ends of the hollow fiber bundle 25, namely on the outer sides of the bulkheads 19, 20 is approximately in the range of 20 to 40%.

Now, the bulkheads 19, 20 will be described below with respect to their formation. As pointed out above, the bulkheads 19, 20 fulfill the important function of separating the interiors of the gas-exchange membranes 2 from the exteriors thereof. Generally, the bulkheads 19, 20 are produced by causing a macromolecular potting material of high polarity such as, for example, polyurethane, silicone, or epoxy resin by the centrifugal casting method into the cavities defined by the inner walls of the opposite ends of the housing 5 curing the cast material. To be more specific, a multiplicity of hollow fiber membranes 2 of a length greater than the length of the housing 15 are prepared, with the openings at the opposite ends thereof provisionally stoppered with highly viscous resin, and are parallelly disposed inside the cylindrical housing body 16 of the housing 15. Then, mold covers of a diameter greater than the diameter of the fixing covers 17, 18 are placed to cover the opposite ends of the gas-exchange membranes 2 completely and, with the housing 15 kept rotated around the axis thereof, the macromolecular potting material is injected inwardly from the opposite ends. When the injection is completed and the resin is cured, the mold covers are removed and the outer end surfaces of the cured resin are cut away with a sharp blade to expose the opposite opening ends of the gas-exchange membranes 2. In this manner, the bulkheads 19, 20 are completed.

The outer surfaces of the bulkheads 19, 20 are covered respectively by flow path forming members 27, 28 each provided with an annular projection. The flow path forming members 27, 28 comprises respectively liquid distributing members 29, 30 and threaded rings 31, 32. The end surfaces of raised strips 33, 34 formed as annular protuberances near the peripheries of the liquid distributing members 29, 30 are held fast respectively against the bulkheads 19, 20 and fixed in position by having helically fitting the threaded rings 31, 32 respectively into the covers 17, 18, with the result that an inflow chamber 35 and an outflow chamber 36 are formed for handling blood as the fluid for transfer of the second substance. In the flow path forming members 27, 28, an inlet 37 and an outlet 38 for the blood as the fluid for transfer of the second substance are formed.

The gaps formed around the peripheries of the bulkheads 19, 20 by the bulkheads 19, 20 and the flow path forming members 27, 28 are sealed tightly with the bulkheads 19, 20 by being filled with packing agents 43, 44 introduced through at least two holes 41, 42 communicating with the gaps. Otherwise, the gaps may be sealed with O-rings (not shown).

In the hollow fiber membrane type artificial lung described above, the fluid for transfer of the first substance is an oxygen-containing gas such as air or blood and the fluid for transfer of the second substance is blood or an oxygen-containing gas. When the fluid for transfer of the first substance is a gas, the fluid for transfer of the second substance is blood. When the fluid for transfer of the first substance is blood, then the fluid for transfer of the second substance is gas.

The present invention has been described with respect to the hollow fiber membrane type artificial lung. In the case of a flat membrane type artificial lung using a plurality of superposed membrane's one coiled membrane, or one membrane folded in a zigzag pattern, when the minute pores in the gas-exchange membrane are similarly blocked with minute particles having a diameter smaller than the pore diameter and having a hydrophobic surface at least on the side intended for exposure to blood, there is obtained a membrane type artificial lung which excels in gas-exchange ability, particularly in the removal of $CO_2$, and avoids inducing any leakage of blood plasma during the course of a protracted use.

Now, the present invention will be described more specifically below with reference to working examples.

EXAMPLE 1 AND CONTROL 1

A hollow fiber membrane type artificial lung 11 having a membrane area of 1.6 $m^2$ and constructed as illustrated in FIG. 7 was assembled using hollow fiber membranes of polypropylene having an inside diameter of 200 $\mu m$, a wall thickness of 25 $\mu m$, a porosity of 45%, and an average pore diameter of 700 Å. Ethanol was introduced through a blood inlet 37 of the hollow fiber membrane type artificial lung 11 and passed through the interior of the artificial lung by way of treatment for impartation of hydrophilicity upon the hollow fiber gas-exchange membranes 2. Then, a dispersion of silica (colloidal silica having an average diameter of 100 Å) in water was introduced through the blood inlet 37 and filtered through the gas-exchange membranes 2 to fill the minute pores of the gas-exchange membranes with silica. Subsequently, distilled water was passed through the hollow fiber gas-exchange membranes until through removal of the aqueous dispersion of silica remaining inside the hollow fiber gas-exchange membranes. Thereafter, the wet membranes were dried. After the drying, a Freon solution containing 2% by weight of methyl hydrogen polysiloxane was passed through the interiors of the gas-exchange membranes. The wet membranes were dried again. Thus, the minute silica particles packed in the minute pores of the gas-exchange membranes were coated with the silicone.

The gas-exchange membranes of the membrane type artificial lung, on observation under an electron microscope (10,000 magnifications), were found to contain virtually no empty pore. Since this artificial lung permitted passage of air as described afterward, it is presumed that the minute pores of the gas-exchange membranes were not completely blocked but still contained extremely minute pores.

The flow volume of air through the membrane type artificial lung (Example 1) obtained as described above was found to be 1,000 ml./min.$m^2$.mmHg, a small value as compared with the flow volume 1,900 ml/min.$m^2$.mmHg, of a membrane type artificial lung existing before the treatment for packing silica particles (Control 1).

For evaluation of performance, the artificial lung was subjected to an in vitro test and an animal test.

1) In vitro test:

A venous blood containing oxygen gas at a partial pressure of 35 mmHg, and carbon dioxide gas at a partial pressure of 45 mmHg, was prepared using a fresh heparin-added bovine blood and passed through the blood path of the artificial lung for evaluation of performance. The bovine blood used in this case had a hemoglobin content of 12 g/dl and a temperature of 37° C.

The relation between the flow volume of blood and the ability to add oxygen gas and the ability to remove carbon dioxide gas when the ratio of the flow volume of oxygen to that of blood was 1 was as shown in Table 1 and FIG. 8.

The relation between the flow volume of oxygen and the ability to remove carbon dioxide gas when the flow volume of blood was 1,500 ml/min. was shown in Table 2 and FIG. 9.

2) Animal test:

With a mongrel dog, the artificial lung was subjected to 30 hour test for extra-corporeal vein-artery circulation of blood. The relation between the circulation test and the amount of blood plasma leakage was as shown in Table 3 and FIG. 10.

CONTROL 2

An artificial lung module having an available membrane surface area of 1.6 $m^2$ was prepared using polypropylene-silicone composite membranes obtained by applying silicone rubber to hollow fibers of polypropylene having an inside diameter of 200 μm, a wall thickness of 25 μm, a porosity of 45%, and an average pore diameter of 700 Å. This artificial lung module was subjected to the in vitro test and the animal test similarly to Example 1 and Control 1. The results are shown in Tables 1–3 and FIGS. 8–10.

TABLE 1

| | Volume of gas transferred (ml/min.) | | | | |
| --- | --- | --- | --- | --- | --- |
| | Flow volume of blood (liter/min.) | | | | |
| | 0 | 0.5 | 1.0 | 1.5 | 2.0 |
| Example 1 | | | | | |
| $CO_2$ | 0 | 32.5 | 60 | 83 | 106 |
| $O_2$ | 0 | 33 | 57 | 74 | 83 |
| Control 1 | | | | | |
| $CO_2$ | 0 | 33 | 64 | 89 | 114 |
| $O_2$ | 0 | 32 | 58 | 76 | 84 |
| Control 2 | | | | | |
| $CO_2$ | 0 | 27 | 45 | 65 | 80 |
| $O_2$ | 0 | 32 | 56 | 75 | 82 |

TABLE 2

| | Volume of $CO_2$ gas transferred (ml/min.) | | | |
| --- | --- | --- | --- | --- |
| | Flow volume of oxygen (liter/min.) | | | |
| | 0 | 5 | 10 | 15 |
| Example 1 | 0 | 153 | 170 | 180 |
| Control 1 | 0 | 162 | 176 | 188 |
| Control 2 | 0 | 98 | 108 | 110 |

TABLE 3

| | Volume of blood leakage (ml/hr.) | | | | | |
| --- | --- | --- | --- | --- | --- | --- |
| | Cumulative time of blood circulations (hr.) | | | | | |
| | 0 | 6 | 12 | 18 | 24 | 30 |
| Example 1 | 0 | 0 | 0 | 0 | 0 | 0 |
| Control 1 | 0 | 0 | 40 | 120 | 300 | 700 |
| Control 2 | 0 | 0 | 0 | 0 | 0 | 0 |

EXAMPLES 2–6 AND CONTROL 3

A hollow fiber membrane type artificial lung 11 having a membrane area of 1.6 m² and constructed as illustrated in FIG. 7 was assembled using hollow fiber membranes of polypropylene having an inside diameter of 200 μm, a wall thickness of 25 μm, a porosity of 45%, and an average pore diameter of 700 Å. Ethanol was introduced through a blood inlet of the hollow fiber membrane type artificial lung by way of treatment for impartation of hydrophilicity. Then a dispersion of silica (colloidal silica having an average diameter of 100 Å) in water was introduced through the blood inlet and filtered through the membranes to fill the minute pores of the gas-exchange membranes with the silica. Subsequently, distilled water was passed through the hollow fiber gas-exchange membranes until through removal of the aqueous dispersion of silica remaining therein. The wet membranes were dried. After the minute pores were blocked with the minute silica particles, a solution having a (methyl methacrylate/butyl methacrylate)-perfluoropropyl acrylate copolymer [weight ratio (25:25):50] dissolved in a varying concentration in a mixed solvent of methylethyl ketone/methyl-isobutyl ketone (volume ratio 4:6 was kept filling the interiors of the hollow fiber gas-exchange membranes for 3 minutes. The membranes were emptied of the solution and swept with air for removal of the solvent to produce a coating.

The gas-exchange membranes of the membrane type artificial lung obtained as described above, on observation under an electron microscope, were found to contain virtually no empty pore. When the membrane artificial lung was tested for air flux, the results were as shown in Table 4, suggesting that the membranes contained extremely minute pores.

For comparison (Control 2), the procedure described above was repeated, except that the packing of minute particles and the coating of resin were omitted. When the resulting artificial lung was tested for air flux, the results were as shown in Table 4.

TABLE 4

| | Concentration of coating solution (% by weight) | Airflux (ml/min · m² · mm Hg) |
| --- | --- | --- |
| Example 2 | 0.5 | 750 |
| Example 3 | 1.0 | 450 |
| Example 4 | 2.0 | 100 |
| Example 5 | 3.0 | 10 |
| Example 6 | 5.0 | 5 |
| Control 2 | — | 1900 |

For evaluation of performance, the artificial lungs mentioned above were subjected to the in vitro test and the animal test by the respective procedures described above.

EXAMPLE 7

The minute pores of the gas-exchange membranes in the hollow fiber membrane type artificial lungs prepared following the procedures of Examples 2–6 were similarly blocked with minute silica particles. Then, a solution in trifluorotrichloroethane (5% by weight) of a two pack (vinyl/methyl siloxane and methylhy/drogen siloxane) type RTV silicone rubber (containing no silica) incorporating therein a chloroplatinic acid catalyst was kept filling the interiors of the hollow fiber gas-exchange membranes for 1 minute. The membrane were emptied of the solution and swept with air for removal of the solvent and were cured at about 60° C. to produce a coating.

The membrane type artificial lung thus obtained was found to have an air flux of 35 ml/min.².mmHg.

Figure 11:
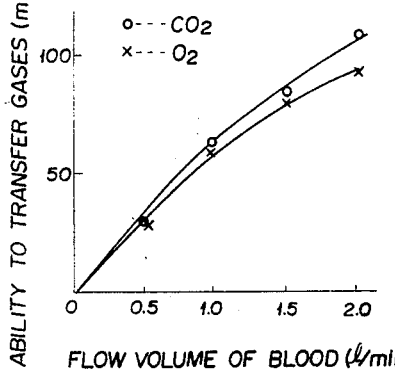
FIG. 11 is a graph showing the relation between the ability to add oxygen gas and the ability to remove carbon dioxide gas on one part and the flow volume of blood through the artificial lung on the other part.
Figure 12:
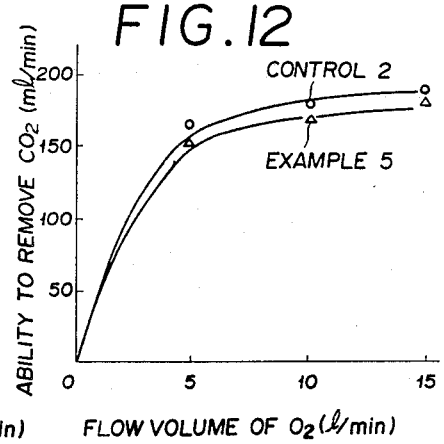
FIG. 12 is a graph showing the relation between the ability to remove carbon dioxide gas and the flow volume of oxygen through the artificial lung.
Figure 13:
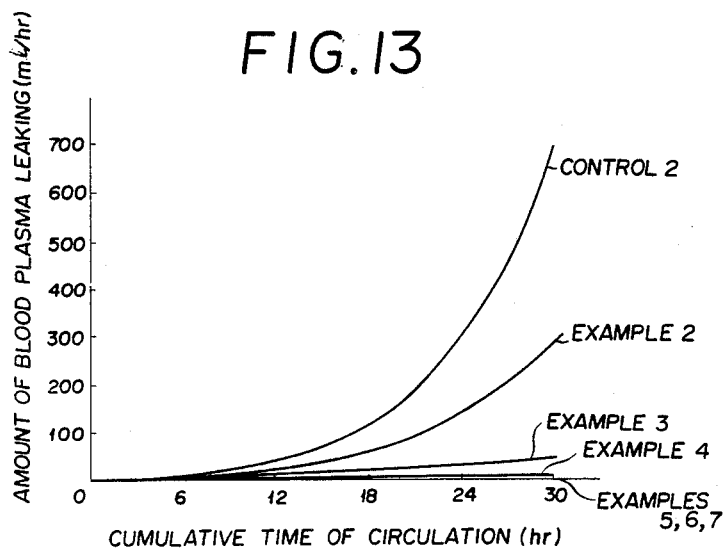
FIG. 13 is a graph showing the relation between the amount of blood plasma leaking and the cumulative time of extra-corporeal circulation of blood.

For evaluation of performance, the artificial lungs mentioned Example 2 to 6 were subjected to the in vitro test and the animal test by the respective procedures described in Example 1. The results were as shown in Tables 5–7 and FIGS. 11–13.

TABLE 5

| | | Volume of gas transferred (ml/min.) | | | | |
| --- | --- | --- | --- | --- | --- | --- |
| | | Flow volume of blood (liter/min.) | | | | |
| | | 0 | 0.5 | 1.0 | 1.5 | 2.0 |
| Example 2 | $CO_2$ | 0 | 32 | 64 | 87 | 110 |
| | $O_2$ | 0 | 32 | 59 | 78 | 86 |
| Example 3 | $CO_2$ | 0 | 33 | 63 | 88 | 112 |
| | $O_2$ | 0 | 30 | 56 | 76 | 81 |
| Example 4 | $CO_2$ | 0 | 31 | 64 | 88 | 111 |
| | $O_2$ | 0 | 32 | 58 | 77 | 84 |
| Example 5 | $CO_2$ | 0 | 32.5 | 60 | 83 | 106 |
| | $O_2$ | 0 | 33 | 57 | 74 | 83 |
| Example 6 | $CO_2$ | 0 | 33 | 62 | 81 | 103 |
| | $O_2$ | 0 | 33 | 57 | 75 | 82 |
| Example 7 | $CO_2$ | 0 | 30 | 58 | 81 | 100 |
| | $O_2$ | 0 | 31 | 52 | 70 | 80 |
| Control 2 | $CO_2$ | 0 | 33 | 64 | 89 | 114 |

TABLE 5-continued

| Volume of gas transferred (ml/min.) | | | | | |
|---|---|---|---|---|---|
| | Flow volume of blood (liter/min.) | | | | |
| | 0 | 0.5 | 1.0 | 1.5 | 2.0 |
| $O_2$ | 0 | 32 | 58 | 76 | 84 |

TABLE 6

| Volume of $CO_2$ gas transferred (ml/min.) | | | | |
|---|---|---|---|---|
| | Flow volume of oxygen (liter/min.) | | | |
| | 0 | 5 | 10 | 15 |
| Example 2 | 0 | 163 | 178 | 186 |
| Example 3 | 0 | 161 | 172 | 183 |
| Example 4 | 0 | 158 | 172 | 184 |
| Example 5 | 0 | 153 | 170 | 180 |
| Example 6 | 0 | 150 | 167 | 176 |
| Example 7 | 0 | 150 | 167 | 173 |
| Control 2 | 0 | 162 | 176 | 188 |

TABLE 7

| | Volume of blood leakage (ml/hr.) Circulation time (hr) | | | | | | Decreasing ratio of platelet (After 30 hrs, %) |
|---|---|---|---|---|---|---|---|
| | 0 | 6 | 12 | 18 | 24 | 30 | |
| Example 2 | 0 | 0 | 20 | 60 | 130 | 300 | 20 |
| Example 3 | 0 | 0 | 5 | 20 | 25 | 30 | 15 |
| Example 4 | 0 | 0 | 0 | 3 | 5 | 5 | 13 |
| Example 5 | 0 | 0 | 0 | 0 | 0 | 0 | 10 |
| Example 6 | 0 | 0 | 0 | 0 | 0 | 0 | 10 |
| Example 7 | 0 | 0 | 0 | 0 | 0 | 0 | 10 |
| Control 2 | 0 | 0 | 40 | 120 | 300 | 700 | 30 |

As described above, this invention is directed to a membrane type artificial lung using as gas-exchange membranes porous hydrophobic membranes having a wall thickness in the range of 5 to 80 μm, a porosity in the range of 20 to 80%, and a pore diameter in the range of 0.01 to 5 μm, which artificial lung is characterized in that the minute pores therein are blocked with minute particles having a diameter smaller than the pore diameter and having a hydrophobic surface at least on the sides thereof intended for exposure to blood. The gas-exchange membranes of this artificial lung, therefore, are inferred as possessing a microporous structure. The artificial lung is excellent in ability to exchange gases, particularly in ability to remove carbon dioxide gas and yet has no possibility of entailing leakage of blood plasma during the course of a protracted use. Thus, it permits removal of the carbon dioxide gas produced in the living body by such low-level extra-corporeal circulation as $ECCO_2R$.

Further, this invention is directed to a membrane type artificial lung using as gas-exchange membranes porous membranes having a wall thickness in the range of 5 to 80 μm, a porosity in the range of 20 to 80%, and a pore diameter in the range of 0.01 to 5 μm, which artificial lung is characterized in that the minute pores in the membranes are blocked with minute particles having a diameter smaller than the pore diameter mentioned above and the gas-exchange membranes are coated with a biocompatible hydrophobic resin at least on the surfaces intended for exposure to blood. The gas-exchange membranes, therefore, are inferred as possessing a microporous structure. This artificial lung is excellent in ability to exchange gases, particularly in ability to remove carbon dioxide gas and yet has no possibility of entailing leakage of blood plasma. Thus, it permits removal of the carbon dioxide gas produced in the living body by such low-level extra-corporeal circulation as $ECCO_2R$. Further, since the inner surfaces of the gas-exchange membranes are coated with biocompatible hydrophobic film on the surface intended for exposure to blood, the damage done to the blood on contact with the membrane type artificial lung during the circulation thereof as manifested in coagulation of blood, formation of microthrombosis, loss of platelets, degeneration of blood plasma proteins, and hemolysis is extremely small.

When the membrane type artificial lung of this invention is fabricated with an air flux of not less than 500 ml/min.m².mmHg, the possibility of the artificial lung suffering from leakage of blood plasma is very remote. When the minute particles are made of silica, the artificial lung's ability to exchange gases, particularly the ability to remove carbon dioxide gas, is especially satisfactory. This artificial lung is also satisfactory in terms of production and cost. When the biocompatible hydrophobic resin is a fluorine-containing resin, desirably a vinyl type copolymer having as one component thereof a vinyl monomer possessing a perfluoroalkyl side chain, preferably a methacrylate type block copolymer having as one component thereof a methacrylate monomer possessing a perfluoroalkyl side chain, the biocompatibility is particularly desirable and the loss of platelets of the blood by contact with the coating is curbed to a great extent. Since the resin of the foregoing description has a very high permeability to gas, the possible degradation of the gas-exchange ability of the gas-exchange membranes owing to the coating is completely repressed. These advantageous properties are particularly conspicuous when the weight ratio in the block copolymer of the polymer component formed of the vinyl monomer possessing the perfluoroalkyl side chain to the polymer component formed of the other monomer of the copolymer falls in the range of 0.25 to 1.5, and when the perfluoroalkyl side chain is —$CH_2CH_2(CF_2)_7CF_3$. When the gas-exchange membranes are made of an olefin type resin, preferably polypropylene, they are excellent in mechanical strength and permits production of a compact membrane type artificial lung.

When the gas-exchange membranes are hollow fiber membranes desirably having an inside diameter in the range of 100 to 1,000 μm and they are made of a polyolefin, preferably polypropylene, the gas-exchange ability is particularly satisfactory. When the minute pores are filled with minute particles having a diameter approximately in the range of 0.003 to 0.5 μm, the possibility of entailing leakage of blood plasma is quite remote.

What is claimed is:

1. A gas-exchange membrane for an artificial lung comprising a porous hydrophobic membrane having a wall thickness in the range of 5 to 80 μm, a porosity in the range of 20 to 80%, and a pore diameter in the range of 0.01 to 5 μm, wherein said porous membrane comprises minute pores blocked with minute particles of silica having a diameter smaller than said pore diameter and having a hydrophobic surface at least on a side exposed to blood, wherein said minute particles have a diameter approximately in the range of 0.003 to 1.0 μm.

2. A gas-exchange membrane for an artificial lung according to claim 1, wherein said porous membrane comprises a plurality of hollow fiber membranes.

3. A gas-exchange membrane for an artificial lung according to claim 2, wherein said hollow fiber membranes have an inside diameter in the range of 100 to 1,000 μm.

4. A gas-exchange membrane for an artificial lung according to claim 1, wherein said minute pores are blocked by being filled with said minute particles.

5. A gas-exchange membrane for an artificial lung according to claim 1, wherein said minute particles are coated with a hydrophobic substance at least on the sides thereof exposed to blood.

6. A gas-exchange membrane for an artificial lung according to claim 1, wherein said porous membrane is made of an olefin type resin.

7. A gas-exchange membrane for an artificial lung according to claim 6, wherein said porous membrane is made of polypropylene.

8. A gas-exchange membrane for an artificial lung comprising a porous hydrophobic membrane having a wall thickness in the range of 5 to 80 μm, a porosity in the range of 20 to 80%, and a pore diameter in the range of 0.01 to 5 μm wherein said porous membrane comprises minute pores blocked with minute particles made of silica and having a diameter smaller than said pore diameter and said porous membrane is coated with a biocompatible hydrophobic resin at least on a side wall exposed to blood, wherein said minute particles have a diameter approximately in the range of 0.003 to 1 μm, and wherein said biocompatible hydrophobic resin forms a coating of a wall thickness in the range of 0.0001 to 10 μm.

9. A gas-exchange membrane for an artificial lung according to claim 8, wherein the air flux of said porous membrane is not more than 500 ml/min.m$^2$.mmHg.

10. A gas-exchange membrane for an artificial lung according to claim 8, wherein said porous membrane comprises a plurality of hollow fiber membranes.

11. A gas-exchange membrane for an artificial lung according to claim 10, wherein said hollow fiber membranes have an inside diameter in the range of 100 to 1,000 μm.

12. A gas-exchange membrane for an artificial lung according to claim 8, wherein said minute pores are blocked by being filled with minute particles.

13. A gas-exchange membrane for an artificial lung according to claim 8, wherein said biocompatible hydrophobic resin is a fluorine-containing resin.

14. A gas-exchange membrane for an artificial lung according to claim 13, wherein said biocompatible hydrophobic resin is a vinyl type copolymer having as one component thereof a vinyl monomer possessing a perfluoroalkyl side chain.

15. A gas-exchange membrane for an artificial lung according to claim 14, wherein said biocompatible hydrophobic resin is a vinyl type block copolymer.

16. A gas-exchange membrane for an artificial lung according to claim 15, wherein said vinyl type block copolymer is a (meth) acrylate type copolymer having at least one component thereof a (meth) acrylate monomer possessing a perfluoroalkyl side chain.

17. A gas-exchange membrane for an artificial lung according to claim 15, wherein the weight ratio in said block copolymer of the polymer component of a vinyl monomer possessing a perfluoroalkyl side chain to the polymer component of the other monomer of said copolymer is in the range of 0.25 to 1.0.

18. A gas-exchange membrane for an artificial lung according to claim 15, wherein said perfluoroalkyl side chain is —$CH_2CH_2(CF_2)_7CF_3$.

19. A gas-exchange membrane for an artificial lung according to claim 8, wherein said porous membrane is made of an olefin type resin.

20. A gas-exchange membrane for an artificial lung according to claim 19, wherein said porous membrane is made of polypropylene.

* * * * *